US011221334B2

(12) United States Patent
Mouchantat

(10) Patent No.: US 11,221,334 B2
(45) Date of Patent: *Jan. 11, 2022

(54) METHOD FOR DETERMINING BREAST CANCER TREATMENT

(71) Applicant: THE REGENTS OF THE UNIVERSITY OF COLORADO, A BODY CORPORATE, Denver, CO (US)

(72) Inventor: Jennifer Richer Mouchantat, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 221 days.

This patent is subject to a terminal disclaimer.

(21) Appl. No.: 16/221,778

(22) Filed: Dec. 17, 2018

(65) Prior Publication Data

US 2019/0113515 A1  Apr. 18, 2019

Related U.S. Application Data

(63) Continuation of application No. 14/423,133, filed as application No. PCT/US2013/031812 on Mar. 15, 2013, now Pat. No. 10,175,240.

(60) Provisional application No. 61/692,331, filed on Aug. 23, 2012.

(51) Int. Cl.
*G01N 33/574* (2006.01)
*G01N 33/74* (2006.01)

(52) U.S. Cl.
CPC ..... *G01N 33/57415* (2013.01); *G01N 33/743* (2013.01); *G01N 2333/723* (2013.01); *G01N 2500/02* (2013.01); *G01N 2500/10* (2013.01); *G01N 2800/52* (2013.01)

(58) Field of Classification Search
CPC ......... G01N 2800/52; G01N 33/57415; G01N 33/743; G01N 2333/723; G01N 2500/02; G01N 2500/10
See application file for complete search history.

(56) References Cited

U.S. PATENT DOCUMENTS

| 5,008,185 | A | 4/1991 | Bacus | |
|---|---|---|---|---|
| 5,292,638 | A | 3/1994 | Benz et al. | |
| 10,175,240 | B2 * | 1/2019 | Mouchantat | ..... G01N 33/57415 |
| 2010/0029734 | A1 | 2/2010 | White et al. | |
| 2015/0253329 | A1 | 9/2015 | Mouchantat | |

FOREIGN PATENT DOCUMENTS

| EP | 2065474 A1 | 6/2009 |
|---|---|---|
| WO | 0200617 A2 | 1/2002 |
| WO | 2007121459 A2 | 10/2007 |
| WO | 2008019375 A9 | 5/2008 |

OTHER PUBLICATIONS

Basu, B. et al., "Preliminary Report of Efficacy of Abiraterone Acetate in Patients with Estrogen (ER) or Androgen Receptor (AR) Positive, Advanced Breast Carcinoma Resistant to Standard Endocrine Therapies," European J Cancer, Supplement, vol. 8(7), Abs. No. 655, 2010, pp. 204-205.
Bryan, et al., "Androgen Receptors in Breast Cancer," Cancer, vol. 54, 1984, pp. 2436-2440.
Carlson, R.W. et al., "Breast Cancer. Clinical Practice Guidelines in Oncology," J Natl Compr Cancer Network, vol. 7, Issue 2, 2009, pp. 122-192.
Cochrane, D.R. et al., "Role of Androgen Receptor in Breast Cancer and Preclinical Analysis of Enzalutamide," Breast Cancer Research, vol. 16, No. 1, 2014, pp. 1-19.
D'Amato, et al., "Cooperative Dynamics of AR and ER Activity in Breast Cancer," Molecular Cancer Research, vol. 14, Issue 11, 2016, pp. 1054-1067.
D'Amato, N.C. et al., "Elucidating the Role of AR in Breast Cancer," Cancer Research, vol. 73, No. 8 Supplement, 2013, pp. 4756.
De Amicis, F. et al., "Androgen Receptor Overexpression Induces Tamoxifen Resistance in Human Breast Cancer Cells," Breast Cancer Res. Treat., vol. 121(1), 2010, pp. 1-11.
Hammond, M.E.H. et al., "American Society of Clinical Oncology/ College of American Pathologists Guideline Recommendations for Immunohistochemical Testing of Estrogen and Progesterone Receptors in Breast Cancer," J Clin Oncology, vol. 28, No. 16, 2010, pp. 2784-2795.
Harvell, D.M.E. et al., "Estrogen Regulated Gene Expression in Response to Neoadjuvant Endocrine Therapy of Breast Cancers: Tamoxifen Agonist Effects Dominate in the Presence of an Aromatase Inhibitor," Breast Cancer Research & Treatment (BCRT), vol. 112, No. 3, 2008, pp. 489-501.

(Continued)

*Primary Examiner* — Hong Sang
(74) *Attorney, Agent, or Firm* — Saul Ewing Arnstein & Lehr LLP; Kathryn Doyle; Domingos J. Silva

(57) ABSTRACT

The present invention provides a method for determining a treatment procedure for breast cancer, a method of predicting a likelihood of success in treating breast cancer, and a method for selecting an endocrine therapy agent for treating breast cancer. In particular, methods of the present invention rely on the amount of androgen receptor (AR) and estrogen receptor (ER) in a tissue sample.

10 Claims, 2 Drawing Sheets

Specification includes a Sequence Listing.

(56) References Cited

OTHER PUBLICATIONS

Hickey, et al., "Evidence for Androgenic Inhibition of Growth in Cultured Human Breast Tumor Tissues Despite a Decrease in the Ratio of Androgen Receptor to Estrogen Receptor Alpha with the Development of Breast Cancer," Endocrine Reviews, vol. 32(3), Supp, Abstract No. OR06-3, 2011.

Hickey, et al., "Minireview: the Androgen Receptor in Breast Tissues: Growth Inhibitor, Tumor Suppressor, Oncogene?," Molecular Endocrinology, vol. 26, Issue 8, 2012, pp. 1252-1267.

Kuenen-Boumeester, et al., "Immunohistochemical Determination of Androgen Receptors in Relation to Oestrogen and Progesterone Receptors in Female Breast Cancer," Int J Cancer, vol. 52, 1992, pp. 581-584.

Moe, R.E. et al., "Androgens and Androgen Receptors: A Clinically Neglected Sector in Breast Cancer Biology," Journal of Surgical Oncology, vol. 95, No. 6, 2007, pp. 437-439.

Nahleh, Z. et al., "Androgen Receptor as a Target for the Treatment of Hormone Receptor-negative Breast Cancer: An Unchartered Territory," Future Oncol, vol. 4(1), 2008, pp. 15-21.

Park, S. et al., "Androgen Receptor Expression is Significantly Associated with Better Outcomes in Estrogen Receptor-Positive Breast Cancers," Annals of Oncology, vol. 22, No. 8, 2011, pp. 1755-1762.

Park, S. et al., "Higher Expression of Androgen Receptor is a Significant Predictor for Better Endocrine-Responsiveness in Estrogen Receptor-Positive Breast Cancers," Breast Cancer Research and Treatment, vol. 133, No. 1, 2012, pp. 311-320.

Peters, A.A. et al., "Androgen Receptor Inhibits Estrogen Receptor Activity and Is Prognostic in Breast Cancer," Cancer Research, vol. 69, No. 15, 2009, pp. 6131-6140.

Rastelli, F. et al., "Factors Predictive of Response to Hormone Therapy in Breast Cancer," Tumori, vol. 94, No. 3, 2008, pp. 370-383.

* cited by examiner

METHOD FOR DETERMINING BREAST CANCER TREATMENT

CROSS-REFERENCE TO RELATED APPLICATIONS

This application is a continuation of, and claims priority to, U.S. patent application Ser. No. 14/423,133, filed Feb. 22, 2015, now issued as U.S. Pat. No. 10,175,240, which is a 35 U.S.C. § 371 National Stage application of, and claims priority to, International Patent Application No. PCT/US2013/031812, filed Mar. 15, 2013, which claims priority under 35 U.S.C. § 119(e) to U.S. Provisional Application No. 61/692,331, filed Aug. 23, 2012, all of which applications are incorporated herein by reference in their entireties.

STATEMENT REGARDING FEDERALLY FUNDED RESEARCH

This invention was made with government support under grant number W81XWM-08-1-0311 awarded by the Army/Medical Research Material and Command. The government has certain rights in the invention.

FIELD OF THE INVENTION

The present invention relates to a method for determining a treatment procedure for breast cancer, a method of predicting a clinical response to a breast cancer treatment, and a method for selecting an endocrine therapy agent in treating breast cancer. In general, methods of the present invention comprise determining the ratio of estrogen receptors (ERs) and androgen receptors (ARs). In particular, the ratio of AR to ER can be used to determine the effective treatment for breast cancer; predict a clinical response to a particular mode of treatment for breast cancer; and select an endocrine therapy agent for treating breast cancer.

BACKGROUND OF THE INVENTION

Breast cancer is an extremely complicated disease. But at its simplest, it can be divided into two types: estrogen receptor (ER) positive breast cancer, which accounts for about 70% of all breast cancers, and ER negative breast cancer. Endocrine therapies, sometimes called hormonal therapies, target the estrogen receptor positive cancer. Thus, in the past, ER has been used as a biomarker to determining whether to treat breast cancer with endocrine therapy or some other non-endocrine based therapy.

Recently it has been shown that in breast cancers, the androgen receptor (AR) is more widely expressed than estrogen receptor (ER) alpha or progesterone receptor (PR). Accordingly, AR has recently emerged as a useful marker for the further refinement of breast cancer subtype classification (1, 2). It has been found that in one particular study involving 2171 invasive breast cancers of women enrolled in the Nurses' Health Study, 77% were positive for AR by immunohistochemistry (IHC) (3). Among the subtypes, 88% of ER+ (i.e., estrogen receptor positive), 59% of HER2+, and 32% of triple negative breast cancers (ER−/PR−/HER2−) were positive for AR expression by IHC (3). Similar to ER and PR, AR expression is associated with a well-differentiated state (4) and more indolent breast cancers (5).

Since ER+ tumors are stimulated by estrogen, therapies such as the ER antagonist tamoxifen or aromatase inhibitors (AIs), which block the conversion of androgens to estrogens, are generally effective for inhibiting the progression of such tumors. However, 30-50% of all ER+ breast cancer patients display de novo resistance to these traditional endocrine therapies and ultimately all metastatic ER+ breast cancers acquire resistance (6, 7).

Interestingly, even among ER+ tumors, some breast cancers respond well to a traditional endocrine therapy while others do not. Currently, there is no reliable method for determining whether a breast cancer will respond better to a traditional endocrine therapy or an anti-androgen therapy. Thus, in most cases, the first line of chemotherapy treatment for breast cancer uses a traditional endocrine therapy, which is effective in only some of the breast cancer patients. As with most chemotherapy treatments, administering a traditional endocrine therapy to those who are not likely to respond positively causes undue physical and financial stress and burden.

Accordingly, there is a need for a method for determining whether a particular breast cancer will respond positively to an endocrine therapy.

SUMMARY OF THE INVENTION

Some aspects of the invention provide methods for determining whether a breast cancer will likely respond to an ER directed therapy or whether it might respond better to an anti-androgen therapy. As used herein the term "ER directed therapy" refers to a chemotherapy that uses a conventional anti-estrogen agent, (e.g., estrogen receptor antagonists such as tamoxifen or fulvestrant) or an aromatase inhibitor (AI) class of drug.

The present invention is based at least in part on the discovery by the present inventor that tumors that respond to a traditional endocrine (i.e., anti-estrogen or AI) therapy have a positive correlation between AR and ER (e.g., when AR is high, ER is also high and when AR is low, ER is also low) while tumors that respond less well to an endocrine therapy (as measured by tumor shrinkage or a shorter time to relapse or shorter disease-free survival) do not exhibit this correlation, or have a significantly more AR than ER (e.g., AR:ER ratio >3, typically >2, and often >1.3).

Some aspects of the invention provide a method for determining the most effective form of endocrine therapy for breast cancer (an ER-directed, i.e., endocrine therapy or an AR directed therapy, e.g., using an AR antagonist). Yet other aspects of the invention provide a method for predicting or monitoring clinical response to a particular mode of breast cancer treatment. Still in other aspects of the invention provide a method for determining which chemotherapy treatment to use on a particular breast cancer patient.

One particular aspect of the invention provides a method for predicting a clinical response of a breast cancer patient to a given mode of treatment.

In general, methods of the invention include determining the ratio of androgen receptor (AR) and estrogen receptor (ER) in a cell sample of the patient. A positive correlation between AR and ER (e.g., when ER is high AR is also high and vice versa) is indicative of a likelihood of a positive response to a traditional ER-directed endocrine therapy (such as anti-estrogens like tamoxifen or fulvestrant, or AIs). In contrast, tumor cells that do not exhibit the positive correlation (or "an inverse correlation)") between AR and ER (for instance an AR:ER ratio of >1.3) is indicative of a likelihood of a positive response to an anti-androgen therapy.

Another aspect of the invention provides a method for determining a treatment procedure for a breast cancer patient. Such a method includes determining the ratio of androgen receptor (AR) and estrogen receptor (ER) in a cell sample of the patient. If there is a positive correlation between AR and ER, then the patient is treated with a traditional endocrine therapy, whereas if there is no positive correlation or an inverse correlation of AR:ER, e.g., the ratio is higher than 1.3, then the patient is treated with an anti-androgen-therapy. Typically, the anti-androgen-therapy comprises administering an androgen receptor inhibitor to the patient suffering from breast cancer, whereas a traditional endocrine therapy comprises administering an estrogen receptor inhibitor (such as tamoxifen or fulvestrant or raloxifen), an aromatase inhibitor, or a combination thereof.

DETAILED DESCRIPTION OF THE INVENTION

Figure 1A:
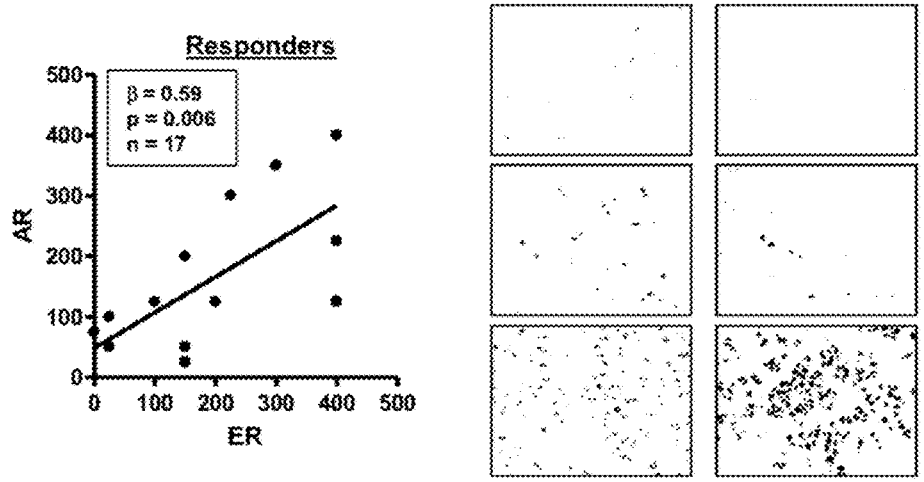
FIGS. 1A-1C show graphs of AR vs. ER in a cell sample and slides of AR and ER immunostaining of breast tumor cells (FIG. 1A and FIG. 1B) and adjacent normal cells (FIG. 1C). Core biopsies from patients were taken prior to receiving four months of neoadjuvant endocrine therapy and stained for AR and ER. Staining score (percent positive staining X intensity) for AR was plotted versus that for ER and shown for patients who responded (FIG. 1A, left), those who did not (FIG. 1B, left), and adjacent normal cells (FIG. 1C, left). The slope of the line ((3) is indicated, as well as the P value, and Spearman correlation. Representative images of AR and ER staining in responders (FIG. 1A, right), non-responders (FIG. 1B, right), and those of adjacent normal cells (FIG. 1C, right) are also shown.

The present inventor discovered that in ER+ tumors that responded to neoadjuvant endocrine therapy, both ER and AR mRNA and protein expression decreased. However, in tumors that failed to respond to endocrine therapy, AR mRNA and protein expression remained elevated (8, 9). Additionally, AR overexpression increased tamoxifen resistance in breast cancer models in vitro and in vivo (10). Interestingly, the present inventor also observed that AR levels increased in response to E2 and also in response to tamoxifen in xenograft tumors. Without being bound to any theory, it is believed that this is an indication that the partial agonist activity of tamoxifen leads to upregulation of AR (8). These data indicate that de novo or acquired resistance to anti-estrogen therapies in breast tumors is a result of a switch from estrogen- to androgen-dependence.

There is a subset of ER negative breast cancers termed molecular apocrine or luminal androgen receptor (LAR) that retain AR (11-14), and the pattern of AR activated gene expression in these tumors closely resembles that of ER+ breast cancers (15, 16). The anti-androgen compound bicalutamide inhibits the growth of molecular apocrine cell lines in vitro and preclinical data in mice with a representative cell line, MDA-MB-453, indicating that anti-androgens can be useful targeted therapies for such tumors (2, 17-20). However, bicalutamide has partial-agonist properties and bicalutamide resistance is a frequent occurrence in prostate cancers (21, 22).

Enzalutamide is a novel AR signaling inhibitor that binds AR with 5-fold higher affinity than bicalutamide, impairs AR nuclear translocation, inhibits DNA binding in prostate cancer cells and lacks agonist activity at effective doses (23-25). Enzalutamide has shown to significantly improve the overall survival in a phase III clinical trial in patients with castration-resistant prostate cancer (CRPC) (26).

Some aspects of the invention provide a method for identifying tumors, in particular breast cancers, that respond to an anti-estrogen therapy, and those that respond better to anti-androgen therapy. As used herein the term "respond" when referring to a particular therapy means that the therapy is effective in treating tumor such that the slowing or arrest of tumor growth or regression of tumor growth (i.e., reduction in tumor) is achieved. As used herein, the term "anti-estrogen therapy" refers to an endocrine therapy using an estrogen receptor (ER) antagonist such as tamoxifen. Other ER antagonists include, ICI or inhibitors of estrogen synthesis such as aromatase inhibitors, as well as those known to one skilled in the art. As used herein, the term "anti-androgen therapy" refers to a therapy using an androgen receptor (AR) antagonist. Exemplary androgen antagonists include enzalutamide, bicalutamide, or inhibitors of the synthesis of androgens such as abiraterone, as well as those known to one skilled in the art. It should be appreciated that the terms "ER antagonists" and "AR antagonists" do not preclude such a compound from active against other receptors. The term merely indicates that the activity of an ER antagonist is more active towards ER than other receptors, such as AR, and similarly an AR antagonist is more active towards AR than other receptors, such as ER. Typically, the activity for a particular receptor is at least twice, often at least five times, and more often at least ten times that of the other receptor.

Aspects of the present invention are based at least in part on the discovery by the present inventor that tumors that respond to anti-estrogen therapy have an ER v. AR relationship along the lines of R-value=0.6397. Alternatively, the ratio of AR:ER in tumors that respond to anti-estrogen therapy is less than 1.3. The ratio of AR:ER can be readily determined by immunostaining. Thus, one can score or determine immunostaining by for AR and ER by multiplying the percentage of cells stained×the intensity of staining. Alternatively, one can simply determine the percentage of cells that stain positively to AR and/or ER. Tumors that do not respond to anti-estrogen therapy were found to have a non-significant relationship or correlation between ER and AR.

Other aspects of the invention provide a method for determining a chemotherapy treatment in accordance with the diagnostic ER v. AR correlation. By determining the ratio of AR:ER using methods described herein, one can select whether to administer an anti-estrogen chemotherapy or an anti-androgen chemotherapy. In general, any methods known to one of ordinary skilled in the art for determining the relative or absolute quantity or value of ER and AR (e.g., mRNA expression level, quantity of mRNA, immunostaining methods such as ELISA and Western blotting) can be used to determine the ratio of ER and AR present in the tumor. In one particular embodiment, immunostaining is used to determine the ratio of AR:ER. Using a method disclosed herein, patients who are found to have tumors with characteristics indicating that they will respond positively to anti-estrogen therapy are treated with anti-estrogen therapy, and patients with tumors that have characteristics indicating that they will not respond positively to anti-estrogen therapy are treated with a different treatment therapy (e.g., an anti-androgen or androgen pathway inhibitor). It should be appreciated that if the analysis indicates anti-estrogen therapy is effective, one can administer a combination of the anti-androgen and anti-estrogen treatments.

Surprisingly and unexpectedly, the present inventor has found that breast cancer tumors having a positive correlation between estrogen receptors and androgen receptors (i.e., when ER is high AR is high and vice versa) are more responsive to traditional endocrine or anti-estrogen therapy (e.g., with tamoxifen or aromatase inhibitors) and that tumors that do not have a positive correlation or tumors that tend to have an inverse correlation between AR and ER do not respond to anti-estrogen therapy. Therefore, tumors that do not have a positive correlation between AR and ER (i.e., having a significantly more AR than ER, e.g., the ratio of AR:ER is 1.3 or higher, typically 2 or higher and often 3 or higher) are candidates for treatment with an anti-androgen or androgen pathway inhibitor. As used herein, the term "positive correlation between AR and ER" refers to the ratio of AR:ER of less than 1.3, typically in the range of between 0.5 and 1.3, and often between 0.7 and 1.3.

In some embodiments, the ratio or correlation of ER versus AR was determined by immunostaining for the estrogen receptor and androgen receptor scores (e.g., percent cells staining×staining intensity). Alternatively, the ratio of AR:ER can be obtained simply by determining the percentage of cells that are positive for immunostaining.

As stated above, aspects of the present invention are based at least in part on the discovery by the present inventor that when these values (e.g., AR and ER immunostaining) were plotted against each other on the same graph, tumors that responded to anti-estrogen therapy has an R value as described herein. In particular, the results of this correlation study showed that tumors that respond to traditional endocrine therapy (with tamoxifen or aromatase inhibitors) had a statistically significant positive correlation between ER and AR (i.e., when ER is high AR tends to be high and vice versa). However, the tumors of patients who did not respond to endocrine therapy did not exhibit the positive correlation; rather they typically showed a trend toward an inverse correlation—with AR score often significantly higher than ER, e.g., the ratio of AR:ER of 1.3 or higher, typically 2 or higher, and often 3 or higher.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Methods

Cell culture. All cell lines used in these studies were authenticated by single tandem repeat analysis. BCK4 cells are a breast cancer cell line derived from a pleural effusion. BCK4 and MCF7 cells were grown in MEM, 5% FBS, NEAA, insulin and penicillin/streptomycin. ZR75 cells were grown in the same media with the addition of HEPES and L-glutamine. T47D cells were grown in DMEM supplemented with 10% FBS, L-glutamine penicillin/streptomycin. LNCaP cells were grown in RPMI, 5% FBS and penicillin/streptomycin. All cells were grown in a 37° C. incubator with 5% $CO_2$. MDA-MB-453 and MDA-kb2, (a derivative of MDA-MB-453 stably expressing the AR-dependent MMTV-luciferase reporter gene construct, ATCC) were cultured in Leibovitz's L-15 media (Invitrogen) containing 10% FBS (Gibco) and penicillin/streptomycin. The MCF7-TGL cells were generated by stable expression of the retroviral SFG-NES-TGL vector, which encodes a triple fusion of thymidine kinase, GFP and luciferase. The cells expressing the fusion protein were sorted for GFP. The identities of all the cell lines were confirmed by DNA profiling using the Identifiler Kit (Applied Biosystems).

Proliferation Assays. MCF7 or BCK4 cells (1000 and 10,000 cells per well, respectively) were plated in a 96-well plate in phenol red-free media containing charcoal stripped serum (CSS). Twenty four hours after plating, cells were treated with a vehicle control (ethanol+DMSO), 10 nM estradiol (E2, Sigma), 10 nM dihydrotestosterone (DHT, Sigma), 1 µM bicalutamide (ChemPacific), 10 µM enzalutamide (Medivation) or combinations of the above. Cells were retreated on day 3. Proliferation was assessed using an MTS assay (as per manufacturer's instructions, Roche). All values are reported as a fold change over the day of treatment (day 0).

Figure 2A:
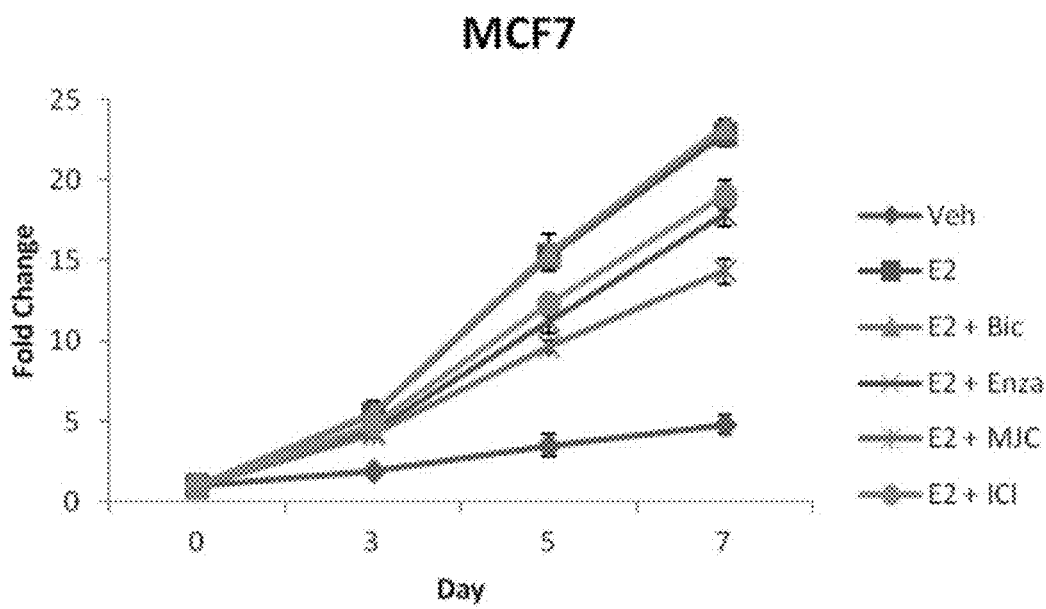
FIGS. 2A and 2B show the result of estrogen-induced proliferation assay.
Figure 2B:
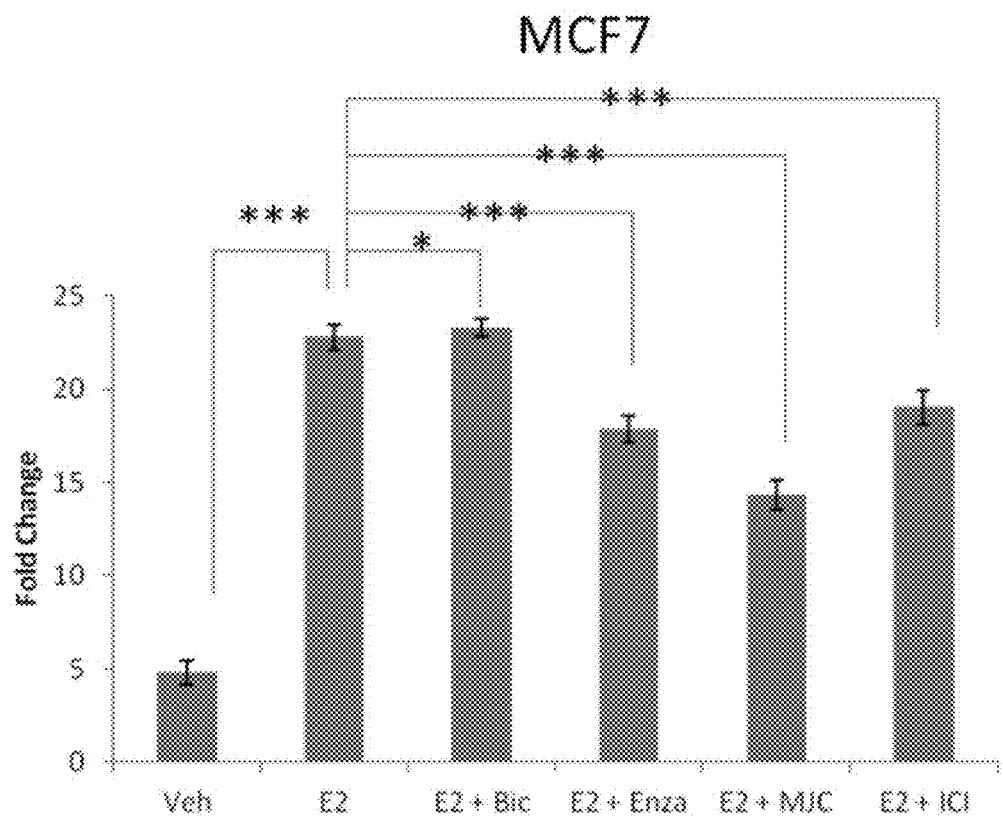

FIGS. 2A-2B show the result of estrogen-induced proliferation assay. MCF7 cells were plated in media containing 5% CSS for 72 h prior to treatment with either vehicle control, 10 nM E2, 10 nM E2+1 uM bicalutamide, 10 nM E2+10 uM Enza, 10 nM E2+30 uM MJC13 (see De Leon, et al., PNAS, 2011, 108(29), 11878-11883), or 10 nM E2+10 nM ICI. Data shown as fold change over time (FIG. 2A) or on Day 7 (FIG. 2B). Error bars represent Std. Dev., *$p<0.05$, ***$p<0.01$ Tumor studies. The MCF7 experiments with enzalutamide (i.e., MDV3100) delivered in rodent chow were performed. The MCF7 and MDA-MB-453 experiments in which enzalutamide was delivered by oral gavage were performed. Briefly, $10^6$ MCF7-TGL cells stably expressing a triple fusion of thymidine kinase, GLP and luciferase (SFG-NES-TGL retroviral vector) for IVIS imaging purposes were mixed with Matrigel (BD Biosciences) and injected into the fourth inguinal mammary fat pad of female, ovariectomized athymic nu/nu or non-obese diabetic (NOD)/SCID mice (Taconic). At time of tumor injection, E2 pellets (60-day release, 1.5 mg/pellet, Innovative Research of America) or DHT (8 mg/pellet, packed and sealed in silastic tubing) were implanted subcutaneously (SQ) at the back of the neck. Tumor burden was assessed using in vivo imaging system (IVIS) or caliper measurements. Once the tumors had established, the mice were matched into groups on the basis of total tumor burden as measured by IVIS or caliper. Groups receiving tamoxifen had a pellet (90-day release, 5 mg/pellet, Innovative Research of America) implanted SQ. Mice were administered enzalutamide in their chow (approximately a 50 mg/kg daily dose) or by oral gavage (10 mg/kg/day or 25 mg/kg/day, Medivation Inc.). Enzalutamide was mixed with ground mouse chow (Cat #AIN-76, Research Diets Inc.; New Brunswick, N.J.) at 0.43 mg per gram of chow. The feed was irradiated and stored at 4° C. before use. Mice in the control group received the same ground mouse chow but without enzalutamide. All mice were given free access to MDV3100 mixed with chow or control chow during the entire study period and at an average of 3.5 g/day food intake. Feed was changed in the animal cages twice a week. Water and feed were prepared ad libitum. Two hours prior to sacrifice, mice were injected IP with 50 mg/kg BrDU (Sigma-Aldrich). Mice were euthanized by $CO_2$ asphyxiation followed by cervical dislocation and blood, tumors, colon, uteri and mammary glands were harvested.

For the MDA-453 tumor study, $6×10^6$ cells were injected into the fourth inguinal mammary fat pad of NOD-SCID-IL2Rgc−/− female mice. A DHT pellet (60-day release, Innovative Research of America) was implanted SQ at the time of cell injection. Tumor size was measured using calipers and once the tumors reached 100 mm³, the mice began receiving 10 mg/kg enzalutamide or vehicle by oral gavage. Once the tumors reached 400 mm³, another group was started on 25 mg/kg enzalutamide. Once the mice were euthanized, tumors were weighed and fixed for immunohistochemical analysis.

Statistical Analysis. Statistics were performed using Graphpad Prism 5.0 software and SAS statistical software (version 9.1). To test for correlation between AR and ER staining, the Spearman correlation was used. When two groups were compared, the Student's t-test (for normally distributed data) or the Wilcoxon rank sum (for non-normally distributed data) were used. A paired t-test or the Wilcoxon sign-rank test was used to compare paired data. For comparison of multiple groups, ANOVA with Bonferroni's multiple comparison test correction (normally distributed data) or the Kruskal-Wallis test with Dunn's multiple comparison test correction (non-normally distributed data) were used. For in vitro data where fold changes calculated for each time point were independent measurements, a two-way fixed effects ANOVA comparing mean fold changes for different day and treatment groups was used. Interaction between fixed terms was tested in the model. A post-test using the Bonferroni t-test was performed to determine which groups differed significantly from each other. Statistical tests were two-sided and a p value of less than 0.05 was considered statistically significant.

Neoadjuvant endocrine therapy study. Inclusion criteria and trial design are described elsewhere (8, 11). Briefly, women with ER+ breast cancers were enrolled in a randomized phase II clinical trial to receive exemestane alone (25 mg daily) or exemestane in combination with tamoxifen (20 mg daily) for four months prior to surgery. Women included in the trial were postmenopausal with newly diagnosed cancers of stage T2-3. Core needle biopsies were taken prior to treatment and tumor pieces from the final excision surgery were taken for analysis. The criteria for "responders" ranged from minor response to complete response, while "non-responders" had stable or progressive disease.

Tamoxifen study. This study includes a subset of the 221 female patients diagnosed with breast cancer at the Massachusetts General Hospital (MGH) between 1977 and 1993, who were treated with adjuvant tamoxifen and followed at MGH through 1998. Archival formalin fixed paraffin embedded tumors in this dataset were paired based on the patient's age at diagnosis, tumor size, tumor grade and nodal status and whether the patient failed tamoxifen treatment within 60 months after treatment started. Because the data on tamoxifen treatment was incomplete, patients without a recorded failure within 60 months of start of treatment were considered not to have failed, while those with a recorded failure within 60 months were classified as failures. Once the paring was completed, it was determined that some of the remaining formalin fixed paraffin embedded tumor slides were not evaluable for AR staining due to the age of the cut slides (10 cases total, 5 in each group). With the cases removed, there was a total of 38 cases remaining in each group for analysis. Therefore this represents a partial matching and was analyzed as a case-control study.

Pearson product moment correlations were used to describe the associations between AR and other variables. Contingency tables were used to study the associations between AR/ER ratio and clinicopathologic variables. In this analysis, each clinicopathologic variable was divided into two or three categories (lymph node negative vs. lymph node positive; lymph node negative vs. one to three positive vs. four or more positive; patient age <50 vs. ≥50 years; tumor size≤2 cm vs. >2 cm; grade 1 vs. 2 vs. 3; progesterone receptor (PgR) negative vs. positive; erbB2≤30% vs. >30%, MIB-1<median vs. ≥median, mitoses/10 high powered fields (MI)<median vs. ≥median, EGFR<median vs. ≥median). AR:ER ratio was calculated using a manual receiver operator characteristic (ROC) analysis where the ratio that produced the best difference between good and poor prognosis in relation to the disease free survival was investigated to identify the cut point for this variable. A Fisher's exact test was used for all dichotomized variables and the chi square for all trichotomized variables to compare the AR:ER ratio with other predictive markers. The Kaplan Meier curves were drawn using the calculated AR:ER ratio. All statistics were calculated using Stat View (Version 5.0, SAS Institute, Cary, N.C.). Significance was determined at p<0.05 and all tests were two-sided.

Immunohistochemistry. Slides were deparaffinized in a series of xylenes and ethanols and antigens were heat retrieved in either 10 mM citrate buffer pH 6.0 (BrdU, Ki67) or 10 mM Tris/1 mM EDTA buffer at pH 9.0 (AR, ER, caspase 3). Tissue for BrdU was incubated in 2N HCl followed by 0.1M sodium borate following antigen retrieval. Antibodies used were: AR clone 441, and ER clone 1D5 (Dakocytomation), cleaved caspase 3 (Cell Signaling Technology), Ki67 (Santa Cruz sc-15402) and BrdU (BD Biosciences). Envision-HRP (Dakocytomation) was used for antibody detection. TUNEL staining for apoptosis was performed using the ApopTag Plus Peroxidase In Situ Apoptosis Detection Kit (Millipore), as per manufacturer's instructions. AR and ER staining was assessed by a pathologist and the score is reported as intensity multiplied by percent positive cells or in the case of the tamoxifen treated cohort, the KM curve is based on percent cells positive, although results are similar and still significant when the intensity is multiplied by percent positive. For BrdU and TUNEL staining in xenograft studies, three separate 200× fields of each xenograft tumor were taken using an Olympus BX40 microscope (Center Valley, Pa.) with a SPOT Insight Mosaic 4.2 camera and software (Diagnostic Instruments, Inc., Sterling Heights, Mich.). A color threshold (RGB for positive staining nuclei, and HSB for total nuclei) was adjusted manually using ImageJ (National Institutes of Health) for each image, and particles created by the thresholds were analyzed for total area. RGB area was divided by HSB area and multiplied by 100 for each image. For analysis of the nuclear androgen receptor, cleaved caspase 3 and Ki67, slides were scanned at 20× on an Aperio Scan ScanScope XT. Mammary tumor tissue was traced separately for each tumor and necrotic areas of the tumor removed using a negative pen tool in Aperio's Scanscope software. A Nuclear Algorithm was utilized to measure the percent positive cells for the Ki-67 and Androgen Receptor stained slides and the data exported. Cleaved Caspase 3 stained slides were analyzed using a modified Positive Pixel Count algorithm.

Immunoblotting. Whole cell protein extracts (50 m) were denatured, separated on SDS PAGE gels and transferred to PVDF membranes. After blocking in 3% BSA in TBS-T, membranes were probed overnight at 4° C. Primary antibodies utilized include: ERα (Neomarkers Ab-16, 1:500 dilution), AR (Upstate PG-21, 1:500 dilution, or Santa Cruz N-20, 1:1000 dilution), GAPDH (Santa Cruz V-18, 1:1000 dilution), Topo 1 (Santa Cruz C-21, 1:1000 dilution) and α-tubulin (clone B-5-1-2 from Sigma, 1:15000 dilution). After incubation with appropriate secondary antibody, results were detected using Western Lightning Chemiluminescence Reagent Plus (Perkin Elmer).

Cellular fractionation. For MDA-MB-453, cellular fractionation analysis was carried out as described in Current Protocols in Cell Biology (57). Briefly, MDA-kb2 cells were washed with ice-cold Dulbecco's phosphate buffered saline (DPBS), pH 7.4, pelleted using centrifugation and resuspended in 2 volumes of ice-cold NSB (10 mM Tris-Cl, pH 7.4, 10 mM NaCl, 2 mM $MgCl_2$, IX protease inhibitors). The volume was adjusted with ice-cold NSB to 15 times the initial volume and incubated for 30 min on ice. The cytoplasmic fraction was obtained by addition of NP-40 to a final concentration of 0.3%. Nuclei and cytoplasm were separated using a 0.4 mm clearance Dounce homogenizer. After centrifugation, the supernatant containing the cytoplasmic fraction was collected. The pellet containing the nuclear fraction was resuspended in a 250 mM sucrose solution containing 10 mM $MgCl_2$ and was then added 1 volume to 880 mM sucrose containing 5 mM $MgCl_2$ under the nuclear fraction. The nuclei were then purified by centrifugation through the sucrose cushion. For MCF7s, cellular fractionation was performed using the NE-PER Nuclear and Cytoplasmic Extraction Kit, as per manufacturer's instructions.

Nuclear Translocation Assay. MDA-kb2 cells were seeded at $2 \times 10^3$ cells/$cm^2$ in optical microplates in Leibovitz's L-15 medium supplemented with 5% CSS. After three days of cultivation the cells were pre-treated with Enza (1 or 10 µM) for 2 h and then co-treated with 1 nM DHT for 1 h in presence of Enza (total 3 h of treatment with Enza). The cells were washed with phosphate buffered saline (PBS), fixed with 4% formaldehyde for 30 min at room temperature and permeabilized with 0.2% triton X-100. Samples were then blocked with 5% BSA for 1 h and incubated with an antibody against AR (AR [N20] Santa Cruz sc-815 1:100) in PBS 0.1% triton overnight. The incubation with the secondary antibody anti-rabbit Alexa Fluor 488 (1:1000) was done in 2.5% BSA for 2 h at ambient temperature. The nuclei were stained with DAPI (1 µg/ml) for 30 min. Cells were visualized with a 60× objective and a Qimaging digital camera coupled to an Olympus X71 fluorescence microscope using a yellow fluorescent protein (YFP) filter (Chroma U-N31040). The nuclear distribution of AR (ratio of nuclear AR signal/total AR signal) was quantified in a minimum of 48 cells using ImageJ software.

Real-Time Quantitative Polymerase Chain Reaction (qPCR). cDNA was synthesized from 1 µg of total RNA, using M-Mulv reverse transcriptase enzyme (Promega). For FASN, PRLR and GCDFP-15, SYBR green quantitative gene expression analysis was performed using the following primers: FASN F 5'-AAGGACCTGTCTAGGTTTGATGC-3' (SEQ ID NO: 1), FASN R 5'-TGGCTTCAT-AGGTGACTTCCA-3' (SEQ ID NO: 2); PRLR F 5'-TAT-TCACTGACTTACCACAGGGA-3' (SEQ ID NO: 3), PRLR R 5'-CCCATCTGGTTAGTGGCATTGA-3' (SEQ ID NO: 4); GCDFP-15 F 5'-TCCCAAGTCAGTACGTC-CAAA-3' (SEQ ID NO: 5), GCDFP-15 R 5'-CTGTTGGTGTAAAAGTCCCAG-3' (SEQ ID NO: 6); 18S F 5'-TTGACGGAAGGGCACCACCAG-3 (SEQ ID NO: 7), 18S R 5'-GCACCACCACCCACGGAATCG-3' (SEQ ID NO: 8). For PR and SDF-1, taqman real time PCR was performed using validated primer/probe sets from Applied Biosystems (assay IDs: PR Hs01556702_ml, SDF-1 Hs00171022 ml, 18S Hs99999901_sl). Relative gene expression was calculated using the comparative Ct method and values were normalized to 18S.

Luciferase Assays. MDA-kb2 cells were plated at $5 \times 10^3$ cells/well in 96-well luminescence plates and incubated overnight. Cells were treated with 10-fold serial dilutions of Enza (10, 1, 0.1 µM) and DHT (10, 1, 0.1, 0.01, 0.001 nM) that were prepared in DMSO. Following 24 h of incubation, the luminescence levels were determined with the luciferase assay system (Promega). Three independent experiments were performed and the luminescence values were determined as relative units (R.U.) and normalized to vehicle. Values were expressed as the mean fold induction±standard error (SE).

Radioligand Binding Assay. The radioligand binding assays were performed by Ricera Biosciences, LLC. ERα or ERβ were incubated with 0.5 nM [$^3$H] Estradiol and unlabeled MDV3100 (enzalutamide) at concentrations ranging from 0.1 µM to 100 µM at 25 C in incubation buffer (10 mM Tris-HCl, 0.1% BSA, 10% glycerol, 1 mM DTT) for 2 hours. $IC_{50}$ values and % inhibition were determined by a non-linear, least squares regression analysis using MathIQ™ (ID Business Solutions Ltd., UK).

Results

Figure 1B:
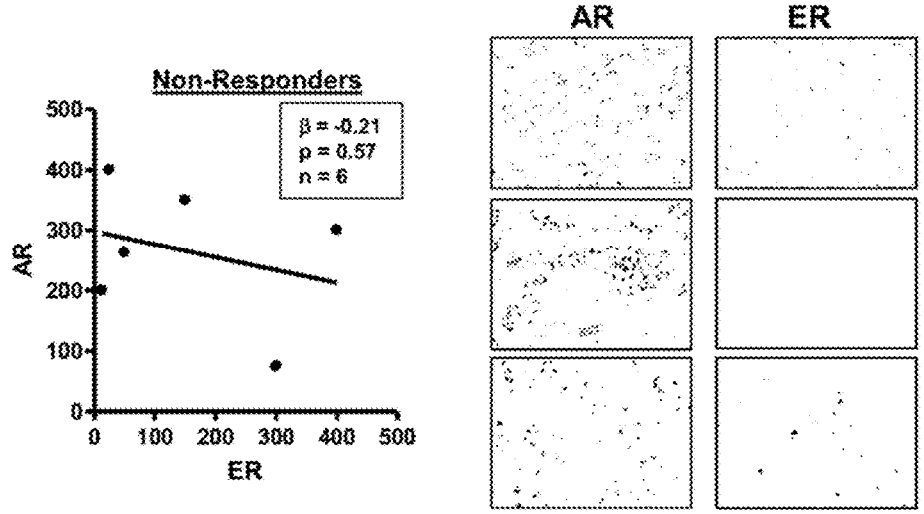

Positive correlation in tumors responsive to neoadjuvant endocrine therapy. AR expression decreased in luminal breast cancers responsive to neoadjuvant AI therapy, but was maintained in tumors that fail to respond (8). To determine if there was a relation between the AR to ER ratio and clinical response, a cohort of patients treated with neoadjuvant AI therapy was examined. In AI responsive tumors there was a strong positive correlation between AR and ER protein expression in pre-treatment biopsies (p=0.006, FIG. 1A, left). In contrast, in tumors that failed to respond there was no significant correlation between AR and ER expression (p=0.59, FIG. 1B, left). Representative images of AR and ER staining in responsive tumors demonstrate similar amounts of the two receptors (FIG. 1A, right), whether low (top), medium (middle) or high (bottom), while non-responsive tumors tend to have higher levels of AR than ER (FIG. 1B, right). Adjacent normal epithelia from both responsive and non-responsive tumors were also examined and scored for AR and ER. The term "adjacent normal epithelia" refers to non-tumor cells that are adjacent to the site of breast tumor.

Figure 1C:
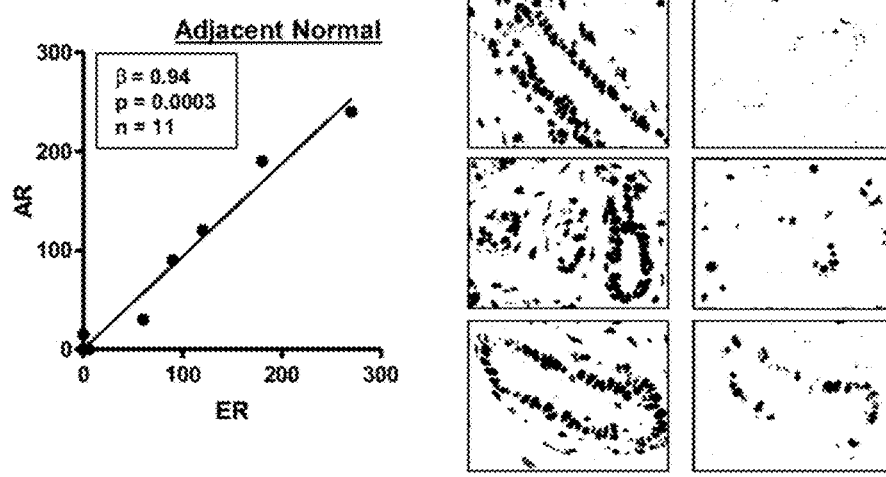

Adjacent normal epithelium also contained a significant positive correlation between the two receptors (p=0.0003, FIG. 1C, left). As in the tumors, a substantial correlation of AR to ER was maintained whether with low, medium or high expression of the receptors (FIG. 1C, right). The median ratio of AR to ER expression in adjacent normal breast epithelial cells was 0.94, in responsive tumors it was 1.00, while in non-responsive tumors the median AR:ER ratio was 3.79 (not shown). Thus, in general the ratio of AR to ER in adjacent normal breast epithelial cell of less than 3, typically, less than 2.5, often less than 2, and more often less than 1.5 is indicative that the breast cancer will respond to an endocrine therapy. Thus, the initial ratio of AR to ER and the maintenance of AR expression following endocrine therapy appear to be determinants of endocrine therapy response. Since AR is also present in the nucleus when bound to ligand, it is believed that AR signaling also plays a role in resistance to therapies directed against ER. This was further indicated by observation that a higher level of AR relative to ER provided de novo or acquired resistance to traditional endocrine therapies that target the ER pathway. This observation also indicates that such breast cancers have switched from dependence on estrogens to being reliant on androgens.

High AR:ER ratio indicates poor response to tamoxifen. To determine if a high amount of AR protein as compared to ER could predict failure to ER-directed therapies, a cohort of tamoxifen treated patients with outcome data was examined. This study included a subset of 221 female patients diagnosed with breast cancer at the Massachusetts General Hospital (MGH) between 1977 and 1993, treated with adjuvant tamoxifen and followed at MGH through 1998. Patients that failed on tamoxifen and those who did not fail were initially matched based on patient's age at diagnosis, tumor size, tumor grade and nodal status. However, some archival tissue had degraded and was removed from the analysis (10 cases total, 5 in each group). After matching and removal of suboptimal cases, a total of 38 cases remained in each group for analysis. Because the sample selection was the result of a partial match, the study was largely analyzed as a case-control study to determine the differences in patient and tumor characteristics between treatment failures and non-failures. An AR:ER ratio of 1.3 was determined to be the point at which there is the best separation between good and poor prognosis. A Kaplan-Meier analysis was performed to examine differences in failure rates by AR:ER ratio status. The group with a higher AR:ER ratio had shorter disease free survival, with a mean time to failure 29+/−4.3 months, compared to the group with AR:ER<1.3 which had mean time to failure 45+/−2.3 months.

When examining the median time to failure (as opposed to the mean reported above), in tumors with AR:ER>=1.3 the median time to failure was 30+/−2 months, while in tumors with AR:ER<1.3 the median time to failure still was not reached at 120 months. The total number of patients who did not fail tamoxifen therapy from the total dataset was approximately three times the number of patients who did fail, while this subset is evenly divided between failures and non-failures. Positive AR staining within the whole cohort of patients negatively correlated with mitotic index and erbB2 expression. However, there were no significant correlations with any of tumor characteristics when separated into low and high AR:ER ratio groups.

Androgens are proliferative in ER+/AR+ breast cancer cell lines and androgen-mediated proliferation can be blocked with an AR signaling inhibitor, such as enzalutamide. Since the clinical data showed that androgen signaling play a role in breast cancer, in vitro models of breast cancer were used to examine androgen-meditated proliferation. AR is widely expressed in luminal breast cancers (3, 27-29), and it was found that in clinical samples, 100% (35/35) of luminal breast tumors expressed AR while only some triple negative breast cancers express AR by 1HC. Lysates from four luminal breast cancer cell lines were probed for AR and ER expression. The prostate cancer cell line LNCaP and the molecular apocrine breast cancer cell line MDA-MB-453, which express high levels of AR, were used as positive controls for AR expression (20, 30, 31). The new androgen receptor signaling inhibitor enzalutamide prevented ligand-mediated stabilization of AR protein. MCF7 cells and the newly derived BCK4 cell line expressed both AR and ER, and both cell lines proliferated in response to DHT in vitro. Studies have demonstrated that MCF7 cells express a wild type AR, albeit with a shortened CAG repeat (32), which is often indicative of a more active receptor (33). To determine if androgen-mediated proliferation in breast cancer cells can be blocked by an anti-androgen, the efficacy of enzalutamide was tested. DHT-stimulated proliferation was blocked by enzalutamide in both cell lines. Furthermore, cellular fractionation revealed that enzalutamide inhibited DHT-mediated nuclear translocation of AR.

To determine if enzalutamide inhibits androgen mediated growth in vivo, MCF7 cells constitutively expressing luciferase (MCF7-TGL) were injected into the mammary fat pad of ovariectomized immunocompromised mice implanted with a DHT pellet. Total tumor burden was measured using whole body luminescent imaging and caliper measurements. Once the tumors were established, mice were matched into two treatment groups (day −2) based on tumor burden as measured by luminescence, one receiving control chow and the other receiving chow containing 50 mg/kg enzalutamide. Tumors in the DHT treated mice continued to grow, while mice receiving DHT+enzalutamide showed regression of the tumors by the in vivo luminescence imaging system (IVIS) and by caliper measurement. On the final day of imaging (day 19) tumors had regressed to near undetectable levels, with an 83.2% decrease in luminescence in mice receiving DHT+enzalutamide as compared to the DHT group. Proliferation in the enzalutamide treated tumors was 31.3% lower than in tumors treated with DHT alone, as determined by BrdU incorporation. Furthermore, TUNEL staining indicated a 50% increase in apoptotic cells in the enzalutamide treated tumors. Consistent with enzalutamide impairing nuclear entry of AR (25), a dramatic decrease (92.5%) in AR nuclear localization was observed in tumors treated with enzalutamide. Similarly, in mice administered enzalutamide by oral gavage, tumor burden decreased in a dose dependent manner.

Enzalutamide inhibits androgen-mediated growth in ER− breast cancer cells in vitro and in vivo. This study was designed to determine whether enzalutamide could block androgen-induced proliferation of AR+ breast cancer cell lines (both ER+ and ER−) in vitro and tumor growth in vivo. Data indicate that enzalutamide not only inhibits androgen-mediated tumor growth of AR+ breast cancers, regardless of ER status, but can also inhibit estrogen-stimulated tumor growth in a preclinical model of ER+/AR+ breast cancer.

Similar to previous reports (3, 34), it was observed that the majority of luminal breast cancers and approximately 25% of ER− breast tumors were positive for AR expression. The ER− cell lines and the ER− tissues displayed a heterogeneous pattern of AR expression. MDA-MB-453 cells represent a molecular apocrine cell line with high levels of AR containing a point mutation with decreased sensitivity to DHT (35). Nonetheless, these cells proliferate in response to androgens (30, 31), and therefore experiments were conducted to determine if enzalutamide could block DHT-mediated effects on gene expression and proliferation. Indeed, enzalutamide substantially completely abrogated proliferation induced by DHT. Expression of androgen/AR-dependent genes fatty acid synthase (FASN), gross cystic disease fluid protein (GCDFP-15) and prolactin receptor (PRLR) (31) was reduced by enzalutamide. Furthermore, in a sub-line of MDA-MB-453 cells that stably express an androgen responsive luciferase reporter (MDA-kb2 (36)), enzalutamide inhibited activation of the luciferase construct in a dose dependent manner. Enzalutamide impairs ligand mediated nuclear import of AR in prostate cells (25). The nuclear to total AR signal was quantified using IHC and cellular fractionation was performed. It was found that the same was true in MDA-MB-453 cells.

To determine if enzalutamide inhibits androgen induced tumor growth, MDA-MB-453 xenografts were grown at the orthotopic site in immunocompromised mice implanted with a DHT pellet. Similar to previous reports (20), DHT stimulated tumor growth. Once the tumors reached 100 mm$^3$, mice were treated with 10 mg/kg/day enzalutamide or vehicle by oral gavage. The mice treated with enzalutamide maintained tumors at substantially the same size as mice not receiving DHT treatment. Another group of mice received a higher dose of enzalutamide (25 mg/kg/day by oral gavage) once the tumors reached 400 mm$^3$. At this higher dose, there was a trend towards decreased tumor size. The weights of the tumors treated with either the low or the high dose of enzalutamide were significantly lower than those of the DHT treated mice, an 85.2% and 65.0% decrease respectively, indicating that the caliper measurements for high dose of enzalutamide underestimates the decreased tumor burden in this group. Interestingly, there was no significant difference in the proliferation rate of any of the groups, as measured by Ki67 staining, but there was a statistically significant increase in apoptosis in both enzalutamide treatment groups versus DHT (60.0% and 54.3% increase in the low and high dose groups respectively), as measured by the amount of cleaved caspase 3. This indicated that in MDA-MB-453 tumors, DHT protects cells against apoptosis and enzalutamide impairs this anti-apoptotic effect. Consistent with the in vitro data, enzalutamide was able to attenuate ligand mediated nuclear entry of AR such that there is a significant decrease (50.0% in the low dose and 44.3% in the high dose group) in the number of AR positive nuclei in the enzalutamide treated tumors. Similarly, when an MDA-MB-453 xenograft study was performed with low and high dose enzalutamide treatments, both initiated when the tumors reached 100 mm$^3$, tumor growth was decreased in a dose dependent manner associated with reduced nuclear AR staining.

Enzalutamide inhibits estrogen mediated growth in vitro and in vivo. Since E2 is the major mitogen in ER+ tumors, a study was conducted to determine whether enzalutamide would affect E2-mediated proliferation in ER+/AR+ breast cancer cells. While enzalutamide has high affinity binding for AR, an in vitro radioligand binding assay showed that enzalutamide did not significantly bind to either ERα or ERβ. However, enzalutamide significantly inhibited E2-induced proliferation of both MCF7 and BCK4 cells in vitro. Enzalutamide also inhibited E2-induced upregulation of PR and stromal cell-derived factor 1 (SDF-1) (also known as CXCL12), two estrogen responsive genes. To determine if other anti-androgens also inhibit E2-mediated proliferation, the effect of bicalutamide on E2-mediated proliferation in vitro was tested. Bicalutamide inhibited DHT mediated proliferation in MCF7 cells, as expected, but in contrast to enzalutamide, significantly increased E2-mediated proliferation. This induction of E2-mediated action was also detected at the gene expression level, where bicalutamide increased the E2-mediated induction of PR and SDF-1 mRNA.

To determine if enzalutamide affects E2-mediated breast tumor growth in vivo, a xenograft study was performed with MCF7-TGL cells constitutively expressing luciferase grown in ovariectomized, immunocompromised mice implanted with an E2 pellet. Cells were injected orthotopically and once the tumors established (average size of 100 mm$^3$), mice were matched into three groups: 1) control chow, 2) control chow and a tamoxifen pellet 3) chow containing 50 mg/kg enzalutamide. Enzalutamide significantly inhibited E2-mediated MCF7 xenograft tumor growth as effectively as tamoxifen, with a decrease in whole body luminescence of 59.9% for the tamoxifen group and 70.3% in the enzalutamide group at day 11. Day 11 was the final day of imaging for the E2 group since the luminescence neared saturation and the mice had to be euthanized due to large tumor burden. The luminescence flux for individual animals was measured and the images of the mice were taken for the day of matching (day −3) and the last imaging day when all the mice were alive (day 11). It was found that both drugs significantly decreased cell proliferation, with a 46.4% decrease in the E2+tamoxifen group and a 54.2% decrease in the E2+enzalutamide group compared to the E2 group, as measured by BrdU incorporation. In contrast to what was observed in DHT-mediated growth, enzalutamide did not induce apoptosis under E2-stimulated growth conditions. These results were recapitulated in xenograft studies in which mice were treated with enzalutamide by oral gavage.

Discussion

Experiments described herein demonstrate that in both MCF-7 cells and a breast cancer line newly derived from a pleural effusion (BCK4), androgens can induce proliferation of ER−/AR+ breast cancers, an observation consistent with previous reports (31, 37-39). In addition, experiments showed that an AR antagonist enzalutamide inhibits androgen-induced growth of both ER+/AR+ and ER−/AR+ breast tumors in vivo. The vast majority of ER+ breast cancers are also AR+ (84-91%) (5, 40, 41) and patients with tumors that co-express AR with ER and PR have a longer disease-free survival than those whose tumors are negative for all three receptors (40), likely because such tumors are more well-differentiated. However, AR is an independent predictor of axillary metastases (41) and correlates with lymph-node positive status (42). Still controversial is how ligand-bound AR affects the proliferation and growth of ER+ breast cancers (43) and if this differs in pre- versus post-menopausal woman when the amount of circulating estrogens differ, or in women with breast cancer being treated with tamoxifen or AI. As disclosed herein, a higher ratio of AR to ER protein is indicative of lack of response to neoadjuvant AI treatment and also shorter disease free survival in patients treated with tamoxifen. These findings show that the AR:ER ratio is novel independent predictor of response to traditional estrogen pathway directed endocrine therapies. The present invention also discloses that patients that relapse while on tamoxifen or AIs are good candidates for AR directed therapy.

In contrast to in vitro data in the ER+/AR+ MCF7 and BCK4 cells that proliferate in response to DHT, in some ER+/AR+ breast cancer cell lines, DHT decreased E2-induced proliferation (30, 44-46). The present inventor has also observed that bicalutamide increased E2-mediated proliferation, indicating that biclalutamide inhibits the ability of AR to decrease ER-mediated proliferation. Combined with the fact that AR is predictive of a better prognosis, these results were taken to indicate that AR is protective against E2-stimulated breast cancer. The present inventor found that the AR signaling inhibitor enzalutamide impairs AR nuclear localization and inhibits E2-mediated proliferation in vitro and in vivo.

Evidence that AR plays a proliferative role in mammary gland development comes from analysis of female mice lacking AR. Mammary gland development is delayed in AR$^{-/-}$ mice, with reduced ductal branching, fewer Cap cells in terminal end buds, decreased lobuloalveolar development, and fewer milk-producing alveoli in lactating glands. Mammary glands of AR$^{-/-}$ mice have 50% less proliferation than glands of AR$^{+/+}$ mice at four and six weeks of age (47). Interestingly, MCF7 cells with AR deleted exhibited a severely impaired proliferative response to E2 and the growth of these cells was inhibited in normal and steroid-deprived media (47).

It is believed that hormonal influences on the breast are quite different in pre-menopausal versus post-menopausal women. Data suggesting a protective effect of androgens come from experiments utilizing androgen in the presence of estrogen, thereby more closely modeling the pre-menopausal state (48). Thus, the theory that androgens and AR are protective against E2-mediated proliferation may be accurate in pre-menopausal women. AR can bind to the ER cofactor FOXA1 and to estrogen response elements (EREs), albeit as a weaker transcriptional activator than ER at these loci. Therefore, the net effect of liganded AR competing with ligand-bound ER may be decreased E2-mediated proliferation (44). Additionally, in ER−/AR+ tumors such as the MDA-MB-453 cell line, global AR binding events reveal a profile largely overlapping that of ER in ER+ luminal A tumors (15). In post-menopausal women with ER+ breast cancer (which represent the majority of cases), and particularly in those being treated with AIs, circulating levels of E2 are extremely low, while circulating androgen levels are relatively high because AIs block the conversion of androgens to estrogen (49). In fact, circulating levels of testosterone, androstenedione, and dehydroepiandrosterone-sulfate (DHEA-S) increase in women on AI therapy (50). In this context, AR is likely able to activate proliferative and anti-apoptotic signaling pathways. Indeed, high levels of the adrenal androgen DHEA-S before treatment are predictive of failure on AIs and circulating DHEA-S increases during treatment in patients with tumors that failed to respond to AI treatment (51).

The present inventor has found that enzalutamide effectively blocks DHT-mediated protection against apoptosis in both ER positive and negative tumors. However, when opposing E2-stimulated tumor growth in ER+/AR+ cells, enzalutamide inhibited proliferation. Although enzalutamide showed only a small competitive binding affinity for ER, it was found that enzalutamide blocks the E2-mediated upregulation of classic ER-regulated genes. The chemokine SDF-1 is induced by E2 and mediates the mitogenic effects of E2 in breast cancer cells (52). Indeed, the SDF-1/CXCR4 pathway activates ER via phosphorylation such that E2-mediated proliferation is blocked by inhibition of this pathway (53). However, whether inhibition of E2-induced SDF-1 is the primary mechanism whereby enzalutamide inhibits E2-mediated proliferation is unclear. Another possibility is that AR is directly involved in E2-mediated proliferation.

In contrast to enzalutamide, bicalutamide enhanced upregulation of E2-regulated genes and enhanced E2-mediated breast cancer cell proliferation in the absence of androgen. This difference in how enzalutamide and bicalutamide affect ER activity is believed to be a result of differences in their mechanism of action. This difference may provide insight into the role of AR in breast cancer. When bound to bicalutamide, AR translocates to the nucleus and binds to DNA; however, transcription is not activated because co-repressors are recruited instead of co-activators (54). In contrast, enzalutamide impairs AR nuclear entry (25, 55). This observation and the fact that enzalutamide blocks E2-induced proliferation and inhibits liganded ER activity on classical ER-regulated genes, suggests that nuclear (and perhaps DNA bound) AR may be critical for ER function. Indeed, AR and ER have been reported to directly interact (56, 57).

Prior to the present disclosure, AR is not used as a biomarker in breast cancer. However, as disclosed herein, it is not the total amounts of ER or AR but rather the ratio that is significant indicator of tumor biology. A high AR to ER ratio is predictive of poor response to endocrine therapy. Without being bound by any theory, this poor response is believed to be a result of de novo and/or acquired resistance to anti-estrogens. Furthermore, higher nuclear expression of AR relative to ER is indicative of active, liganded AR, since AR protein translocates to the nucleus and is stabilized upon ligand binding. The present disclosure shows that AR and ER protein are expressed at roughly equivalent amounts in tumors that respond to neoadjuvant endocrine therapy and in adjacent uninvolved epithelium, indicating that close to equal levels of AR and ER reflect a more normal or well-differentiated state. In addition to being an indicator of response to ER-directed therapies, high levels of AR relative to ER also indicate tumors that would benefit from an anti-androgen therapy such as enzalutamide.

While AR has been considered as a potential therapeutic target in ER−/AR+ breast cancers (13, 14, 16, 20), it has not previously been suggested as a target in ER+ breast cancers. However, since some ER+ breast cancer patients ultimately fail on traditional anti-estrogen directed therapies, targeting AR to inhibit androgen-stimulated tumor growth, or as an alternative/additional way to inhibit E2-mediated growth, can be very useful clinically. Further, a high AR to ER ratio indicates a subset of breast cancers that would respond more favorably to anti-androgen therapy (e.g., using enzalutamide) than an anti-estrogen directed therapy or at least indicate that such tumors benefit from an anti-androgen compound, such as enzalutamide, upon relapse while on traditional ER-directed therapies. It was observed that even in MCF-7 xenografts, which express more ER than AR, enzalutamide was as effective as tamoxifen in inhibiting tumor growth. Taken together, data presented herein support a role for AR in resistance to traditional endocrine therapy, particularly in post-menopausal women. Further, data disclosed herein indicate using an anti-androgen compound or AR antagonist, such as enzalutamide, for treatment of $AR^+$ tumors regardless of ER status, since this drug has the ability to block both androgen- and estrogen-mediated tumor growth.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

REFERENCES

1. Guedj, M., Marisa, L., de Reynies, A., Orsetti, B., Schiappa, R., Bibeau, F., Macgrogan, G., Lerebours, F., Finetti, P., Longy, M., et al. 2011. A refined molecular taxonomy of breast cancer. Oncogene.
2. Lehmann, B. D., Bauer, J. A., Chen, X., Sanders, M. E., Chakravarthy, A. B., Shyr, Y., and Pietenpol, J. A. 2011. Identification of human triple-negative breast cancer subtypes and preclinical models for selection of targeted therapies. J Clin Invest 121.
3. Collins, L. C., Cole, K. S., Marotti, J. D., Hu, R., Schnitt, S. J., and Tamimi, R. M. 2011. Androgen receptor expression in breast cancer in relation to molecular phenotype: results from the Nurses' Health Study. Mod Pathol 24:924-931.
4. Park, S., Koo, J., Park, H. S., Kim, J. H., Choi, S. Y., Lee, J. H., Park, B. W., and Lee, K. S. 2010. Expression of androgen receptors in primary breast cancer. Ann Oncol 21:488-492.

5. Hu, R., Dawood, S., Holmes, M. D., Collins, L. C., Schnitt, S. J., Cole, K., Marotti, J. D., Hankinson, S. E., Colditz, G. A., and Tamimi, R. M. 2011. Androgen receptor expression and breast cancer survival in postmenopausal women. Clin Cancer Res 17: 1867-1874.
6. Bergh, J., Jonsson, P. E., Lidbrink, E. K., Trudeau, M., Eiermann, W., Brattstrom, D., Lindemann, J. P., Wiklund, F., and Henriksson, R. 2012. FACT: An Open-Label Randomized Phase III Study of Fulvestrant and Anastrozole in Combination Compared With Anastrozole Alone as First-Line Therapy for Patients With Receptor-Positive Postmenopausal Breast Cancer. J Clin Oncol.
7. Mouridsen, H., Gershanovich, M., Sun, Y., Perez-Carrion, R., Boni, C., Monnier, A., Apffelstaedt, J., Smith, R., Sleeboom, H. P., Jaenicke, F., et al. 2003. Phase III study of letrozole versus tamoxifen as first-line therapy of advanced breast cancer in postmenopausal women: analysis of survival and update of efficacy from the International Letrozole Breast Cancer Group. J Clin Oncol 21:2101-2109.
8. Harvell, D. M., Richer, J. K., Singh, M., Spoelstra, N., Finlayson, C., Borges, V. F., Elias, A. D., and Horwitz, K. B. 2008. Estrogen regulated gene expression in response to neoadjuvant endocrine therapy of breast cancers: tamoxifen agonist effects dominate in the presence of an aromatase inhibitor. Breast Cancer Res Treat.
9. Harvell, D. M., Spoelstra, N. S., Singh, M., McManaman, J. L., Finlayson, C., Phang, T., Trapp, S., Hunter, L., Dye, W. W., Borges, V. F., et al. 2008. Molecular signatures of neoadjuvant endocrine therapy for breast cancer: characteristics of response or intrinsic resistance. Breast Cancer Res Treat.
10. De Amicis, F., Thirugnansampanthan, J., Cui, Y., Selever, J., Beyer, A., Parra, I., Weigel, N. L., Herynk, M. H., Tsimelzon, A., Lewis, M. T., et al. 2010. Androgen receptor overexpression induces tamoxifen resistance in human breast cancer cells. Breast Cancer Res Treat 121: 1-11.
11. Niemeier, L. A., Dabbs, D. J., Beriwal, S., Striebel, J. M., and Bhargava, R. 2010. Androgen receptor in breast cancer: expression in estrogen receptor-positive tumors and in estrogen receptor-negative tumors with apocrine differentiation. Mod Pathol 23:205-212.
12. Tsutsumi, Y. 2012. Apocrine Carcinoma as Triple-negative Breast Cancer: Novel Definition of Apocrine-type Carcinoma as Estrogen/Progesterone Receptor-negative and Androgen Receptor-positive Invasive Ductal Carcinoma. Jpn J Clin Oncol 42:375-386.
13. Doane, A. S., Danso, M., Lai, P., Donaton, M., Zhang, L., Hudis, C., and Gerald, W. L. 2006. An estrogen receptor-negative breast cancer subset characterized by a hormonally regulated transcriptional program and response to androgen. Oncogene 25:3994-4008.
14. Farmer, P., Bonnefoi, H., Becette, V., Tubiana-Hulin, M., Fumoleau, P., Larsimont, D., Macgrogan, G., Bergh, J., Cameron, D., Goldstein, D., et al. 2005. Identification of molecular apocrine breast tumours by microarray analysis. Oncogene 24:4660-4671.
15. Robinson, J. L., Macarthur, S., Ross-Innes, C. S., Tilley, W. D., Neal, D. E., Mills, I. G., and Carroll, J. S. 2011. Androgen receptor driven transcription in molecular apocrine breast cancer is mediated by FoxA1. Embo J 30:3019-3027.
16. Lehmann, B. D., Bauer, J. A., Chen, X., Sanders, M. E., Chakravarthy, A. B., Shyr, Y., and Pietenpol, J. A. 2011. Identification of human triple-negative breast cancer subtypes and preclinical models for selection of targeted therapies. J Clin Invest 121:2750-2767.
17. Garay, J. P., Karakas, B., Abukhdeir, A. M., Cosgrove, D. P., Gustin, J. P., Higgins, M. J., Konishi, H., Konishi, Y., Lauring, J., Mohseni, M., et al. 2012. The growth response to androgen receptor signaling in ERalpha-negative human breast cells is dependent on p21 and mediated by MAPK activation. Breast Cancer Res 14:R27.
18. Gucalp, A., and Traina, T. A. 2010. Triple-negative breast cancer: role of the androgen receptor. Cancer J 16:62-65.
19. Naderi, A., Chia, K. M., and Liu, J. 2011. Synergy between inhibitors of androgen receptor and MEK has therapeutic implications in estrogen receptor-negative breast cancer. Breast Cancer Res 13:R36.
20. Ni, M., Chen, Y., Lim, E., Wimberly, H., Bailey, S. T., Imai, Y., Rimm, D. L., Liu, X. S., and Brown, M. 2011. Targeting androgen receptor in estrogen receptor-negative breast cancer. Cancer Cell 20: 119-131.
21. Clegg, N. J., Wongvipat, J., Joseph, J. D., Tran, C., Ouk, S., Dilhas, A., Chen, Y., Grillot, K., Bischoff, E. D., Cai, L., et al. 2012. ARN-509: a novel antiandrogen for prostate cancer treatment. Cancer Res 72: 1494-1503.
22. Pal, S. K., Twardowski, P., and Josephson, D. Y. 2009. Beyond castration and chemotherapy: novel approaches to targeting androgen-driven pathways. Maturitas 64:61-66.
23. Scher, H. I., Buchanan, G., Gerald, W., Butler, L. M., and Tilley, W. D. 2004. Targeting the androgen receptor: improving outcomes for castration-resistant prostate cancer. Endocr Relat Cancer 11:459-476.
24. Scher, H. I., Halabi, S., Tannock, I., Morris, M., Sternberg, C. N., Carducci, M. A., Eisenberger, M. A., Higano, C., Bubley, G. J., Dreicer, R., et al. 2008. Design and end points of clinical trials for patients with progressive prostate cancer and castrate levels of testosterone: recommendations of the Prostate Cancer Clinical Trials Working Group. J Clin Oncol 26: 1148-1159.
25. Tran, C., Ouk, S., Clegg, N. J., Chen, Y., Watson, P. A., Arora, V., Wongvipat, J., Smith-Jones, P. M., Yoo, D., Kwon, A., et al. 2009. Development of a second-generation antiandrogen for treatment of advanced prostate cancer. Science 324:787-790.
26. Scher, H. I., Fizazi, F., Saad, M. E., Taplin, C. N., Sternberg, K., Miller, R., De Wit, P., Mulers, M., Hirmand, B., Selby, J. S., et al. 2012. MDV3100 Improves Overall Survival in Men with Prostate Cancer Post-Docetaxel Results from the Phase 3 AFFIRM Study. J Clin Oncol 30.
27. Castellano, I., Allia, E., Accortanzo, V., Vandone, A. M., Chiusa, L., Arisio, R., Durando, A., Donadio, M., Bussolati, G., Coates, A. S., et al. 2010. Androgen receptor expression is a significant prognostic factor in estrogen receptor positive breast cancers. Breast Cancer Res Treat 124:607-617.
28. Yu, Q., Niu, Y., Liu, N., Zhang, J. Z., Liu, T. J., Zhang, R. J., Wang, S. L., Ding, X. M., and Xiao, X. Q. 2011. Expression of androgen receptor in breast cancer and its significance as a prognostic factor. Ann Oncol 22:1288-1294.
29. Ogawa, Y., Hai, E., Matsumoto, K., Ikeda, K., Tokunaga, S., Nagahara, H., Sakurai, K., Inoue, T., and Nishiguchi, Y. 2008. Androgen receptor expression in breast cancer: relationship with clinicopathological factors and biomarkers. Int J Clin Oncol 13:431-435.

30. Birrell, S. N., Bentel, J. M., Hickey, T. E., Ricciardelli, C., Weger, M. A., Horsfall, D. J., and Tilley, W. D. 1995. Androgens induce divergent proliferative responses in human breast cancer cell lines. J Steroid Biochem Mol Biol 52:459-467.
31. Hall, R. E., Birrell, S. N., Tilley, W. D., and Sutherland, R. L. 1994. MDA-MB-453, an androgen-responsive human breast carcinoma cell line with high level androgen receptor expression. Eur J Cancer 30A:484-490.
32. Magklara, A., Brown, T. J., and Diamandis, E. P. 2002. Characterization of androgen receptor and nuclear receptor co-regulator expression in human breast cancer cell lines exhibiting differential regulation of kallikreins 2 and 3. IntJ Cancer 100:507-514.
33. Chamberlain, N. L., Driver, E. D., and Miesfeld, R. L. 1994. The length and location of CAG trinucleotide repeats in the androgen receptor N-terminal domain affect transactivation function. Nucleic Acids Res 22:3181-3186.
34. Subik, K., Lee, J. F., Baxter, L., Strzepek, T., Costello, D., Crowley, P., Xing, L., Hung, M. C., Bonfiglio, T., Hicks, D. G., et al. 2010. The Expression Patterns of ER, PR, HER2, CK5/6, EGFR, Ki-67 and AR by Immunohistochemical Analysis in Breast Cancer Cell Lines. Breast Cancer (Auckl) 4:35-41.
35. Moore, N. L., Buchanan, G., Harris, J., Selth, L. A., Bianco-Miotto, T., Hanson, A. R., Birrell, S., Butler, L. M., Hickey, T., and Tilley, W. D. 2012. An androgen receptor mutation in the MDA-MB-453 cell line model of molecular apocrine breast cancer compromises receptor activity. Endocr Relat Cancer.
36. Wilson, V. S., Bobseine, K., Lambright, C. R., and Gray, L. E., Jr. 2002. A novel cell line, MDA-kb2, that stably expresses an androgen- and glucocorticoid-responsive reporter for the detection of hormone receptor agonists and antagonists. Toxicol Sci 66:69-81.
37. Sikora, M. J., Cordero, K. E., Larios, J. M., Johnson, M. D., Lippman, M. E., and Rae, J. M. 2009. The androgen metabolite 5alpha-androstane-3beta,17beta-diol (3betaA-diol) induces breast cancer growth via estrogen receptor: implications for aromatase inhibitor resistance. Breast Cancer Res Treat 115:289-296.
38. Szelei, J., Jimenez, J., Soto, A. M., Luizzi, M. F., and Sonnenschein, C. 1997. Androgen-induced inhibition of proliferation in human breast cancer MCF7 cells transfected with androgen receptor. Endocrinology 138: 1406-1412.
39. Lin, H. Y., Sun, M., Lin, C., Tang, H. Y., London, D., Shih, A., Davis, F. B., and Davis, P. J. 2009. Androgen-induced human breast cancer cell proliferation is mediated by discrete mechanisms in estrogen receptor-alpha-positive and -negative breast cancer cells. J Steroid Biochem Mol Biol 113:182-188.
40. Kuenen-Boumeester, V., Van der Kwast, T. H., Claassen, C. C., Look, M. P., Liem, G. S., Klijn, J. G., and Henzen-Logmans, S. C. 1996. The clinical significance of androgen receptors in breast cancer and their relation to histological and cell biological parameters. Eur J Cancer 32A: 1560-1565.
41. Soreide, J. A., Lea, O. A., Varhaug, J. E., Skarstein, A., and Kvinnsland, S. 1992. Androgen receptors in operable breast cancer: relation to other steroid hormone receptors, correlations to prognostic factors and predictive value for effect of adjuvant tamoxifen treatment. Eur J Surg Oncol 18: 112-118.
42. Agoff, S. N., Swanson, P. E., Linden, H., Hawes, S. E., and Lawton, T. J. 2003. Androgen receptor expression in estrogen receptor-negative breast cancer. Immunohistochemical, clinical, and prognostic associations. Am J Clin Pathol 120:725-731.
43. Hickey, T. E., Robinson, J. L., Carroll, J. S., and Tilley, W. D. 2012. Minireview: The Androgen Receptor in Breast Tissues: Growth Inhibitor, Tumor Suppressor, Oncogene? Mol Endocrinol.
44. Peters, A. A., Buchanan, G., Ricciardelli, C., Bianco-Miotto, T., Centenera, M. M., Harris, J. M., Jindal, S., Segara, D., Jia, L., Moore, N. L., et al. 2009. Androgen receptor inhibits estrogen receptor-alpha activity and is prognostic in breast cancer. Cancer Res 69:6131-6140.
45. Poulin, R., Baker, D., and Labrie, F. 1988. Androgens inhibit basal and estrogen-induced cell proliferation in the ZR-75-1 human breast cancer cell line. Breast Cancer Res Treat 12:213-225.
46. Macedo, L. F., Guo, Z., Tilghman, S. L., Sabnis, G. J., Qiu, Y., and Brodie, A. 2006. Role of androgens on MCF-7 breast cancer cell growth and on the inhibitory effect of letrozole. Cancer Res 66:7775-7782.
47. Yeh, S., Hu, Y. C., Wang, P. H., Xie, C., Xu, Q., Tsai, M. Y., Dong, Z., Wang, R. S., Lee, T. H., and Chang, C. 2003. Abnormal mammary gland development and growth retardation in female mice and MCF7 breast cancer cells lacking androgen receptor. J Exp Med 198:1899-1908.
48. Cops, E. J., Bianco-Miotto, T., Moore, N. L., Clarke, C. L., Birrell, S. N., Butler, L. M., and Tilley, W. D. 2008. Antiproliferative actions of the synthetic androgen, mibolerone, in breast cancer cells are mediated by both androgen and progesterone receptors. J Steroid Biochem Mol Biol 110:236-243.
49. Dimitrakakis, C., and Bondy, C. 2009. Androgens and the breast. Breast Cancer Res 11:212.
50. Gallicchio, L., Macdonald, R., Wood, B., Rushovich, E., and Helzlsouer, K. J. 2011. Androgens and musculoskeletal symptoms among breast cancer patients on aromatase inhibitor therapy. Breast Cancer Res Treat.
51. Morris, K. T., Toth-Fejel, S., Schmidt, J., Fletcher, W. S., and Pommier, R. F. 2001. High dehydroepiandrosterone-sulfate predicts breast cancer progression during new aromatase inhibitor therapy and stimulates breast cancer cell growth in tissue culture: a renewed role for adrenalectomy. Surgery 130:947-953.
52. Hall, J. M., and Korach, K. S. 2003. Stromal cell-derived factor 1, a novel target of estrogen receptor action, mediates the mitogenic effects of estradiol in ovarian and breast cancer cells. Mol Endocrinol 17:792-803.
53. Sauve, K., Lepage, J., Sanchez, M., Heveker, N., and Tremblay, A. 2009. Positive feedback activation of estrogen receptors by the CXCL12-CXCR4 pathway. Cancer Res 69:5793-5800.
54. Masiello, D., Cheng, S., Bubley, G. J., Lu, M X., and Balk, S. P. 2002. Bicalutamide functions as an androgen receptor antagonist by assembly of a transcriptionally inactive receptor. J Biol Chem 277:26321-26326.
55. Kang, Z., Janne, O. A., and Palvimo, J. J. 2004. Coregulator recruitment and histone modifications in transcriptional regulation by the androgen receptor. Mol Endocrinol 18:2633-2648.
56. Panet-Raymond, V., Gottlieb, B., Beitel, L. K., Pinsky, L., and Trifiro, M. A. 2000. Interactions between androgen and estrogen receptors and the effects on their transactivational properties. Mol Cell Endocrinol 167: 139-150.
57. Migliaccio, A., Di Domenico, M., Castoria, G., Nanayakkara, M., Lombardi, M., de Falco, A., Bilancio, A., Varricchio, L., Ciociola, A., and Auricchio, F. 2005. Steroid receptor regulation of epidermal growth factor signaling through Src in breast and prostate cancer cells: steroid antagonist action. Cancer Res 65: 10585-10593

What is claimed is:

1. A method for treating patients suffering from breast cancer, the method comprising:
identifying the presence of a positive correlation between androgen receptor (AR) and estrogen receptor (ER) by determining a ratio of AR-positive cells to ER-positive cells in breast cancer tissue samples of the patients; wherein:
if the ratio is between 0.5 and 1.3 then the positive correlation is present and
if the ratio is greater than 1.3 then the positive correlation is absent; and
i) administering to the patients having the positive correlation an anti-estrogen therapeutic agent, and
ii) administering to the patients lacking the positive correlation an anti-androgen therapeutic agent.

2. The method of claim 1, wherein the positive correlation between AR and ER comprises having a ratio of AR-positive cells to ER-positive cells ranging from about 0.45 to about 0.85 in the tissue samples.

3. The method of claim 1, wherein the positive correlation between AR and ER comprises having a ratio of AR-positive cells to ER-positive cells ranging from about 0.55 to about 0.75 in the tissue samples.

4. The method of claim 1, wherein the tissue samples further comprises adjacent epithelium.

5. The method of claim 1, wherein the step of determining the ratio of AR-positive cells and ER-positive cells in the tissue samples comprises immunostaining the tissue samples.

6. The method of claim 1, wherein the step of determining the ratio of AR-positive cells and ER-positive cells in the tissue samples comprises determining the percentage of cells stained by immunostaining.

7. The method of claim 6, where the step of determining the ratio of AR-positive cells and ER-positive cells in the tissue samples further comprises determining the intensity of staining of cells stained by immunostaining.

8. The method of claim 1, wherein the anti-androgen therapeutic agent comprises an AR inhibitor or inhibitor of androgen synthesis.

9. The method of claim 1, wherein the anti-estrogen therapeutic agent comprises an ER inhibitor or estrogen synthesis inhibitor.

10. The method of claim 9, wherein the anti-estrogen therapeutic agent comprises tamoxifen, an aromatase inhibitor, or a combination thereof.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: FASN PCR Forward Primer Sequence

<400> SEQUENCE: 1
aaggacctgt ctaggtttga tgc                                    23

<210> SEQ ID NO 2
<211> LENGTH: 21
<212> TYPE: DNA
<213> ORGANISM: Artificial Sequence
<220> FEATURE:
<223> OTHER INFORMATION: FASN PCR Reverse Primer

<400> SEQUENCE: 2
tggcttcata ggtgacttcc a                                      21

<210> SEQ ID NO 3
<211> LENGTH: 23
<212> TYPE: DNA
<213> ORGANISM: Artificial Sequence
<220> FEATURE:
<223> OTHER INFORMATION: PRLR PCR Forward Primer

<400> SEQUENCE: 3
tattcactga cttaccacag gga                                    23

<210> SEQ ID NO 4
<211> LENGTH: 22
<212> TYPE: DNA
<213> ORGANISM: Artificial Sequence
<220> FEATURE:
<223> OTHER INFORMATION: PRLR PCR Reverse Primer

<400> SEQUENCE: 4
cccatctggt tagtggcatt ga                                     22

<210> SEQ ID NO 5
<211> LENGTH: 21
<212> TYPE: DNA
<213> ORGANISM: Artificial Sequence
<220> FEATURE:
<223> OTHER INFORMATION: GCDFP-15 PCR Forward Primer

<400> SEQUENCE: 5
tcccaagtca gtacgtccaa a                                      21

<210> SEQ ID NO 6
<211> LENGTH: 21
<212> TYPE: DNA
<213> ORGANISM: Artificial Sequence
<220> FEATURE:
<223> OTHER INFORMATION: GCDFP-15 PCR Reverse Primer

<400> SEQUENCE: 6
ctgttggtgt aaaagtccca g                                      21

<210> SEQ ID NO 7
<211> LENGTH: 21
<212> TYPE: DNA
<213> ORGANISM: Artificial Sequence

```
<220> FEATURE:
<223> OTHER INFORMATION: 18S PCR Forward Primer

<400> SEQUENCE: 7
ttgacggaag ggcaccacca g                                           21

<210> SEQ ID NO 8
<211> LENGTH: 21
<212> TYPE: DNA
<213> ORGANISM: Artificial Sequence
<220> FEATURE:
<223> OTHER INFORMATION: 18S PCR Reverse Primer

<400> SEQUENCE: 8
gcaccaccac ccacggaatc g                                           21
```